United States Patent [19]

Maffrand

[11] 4,248,890
[45] Feb. 3, 1981

[54] L-CYSTEINE DERIVATIVES AND MEDICAMENTS CONTAINING THEM

[75] Inventor: Jean-Pierre Maffrand, Portet-sur-Garonne, France

[73] Assignee: Parcor, Paris, France

[21] Appl. No.: 45,771

[22] Filed: Jun. 5, 1979

[30] Foreign Application Priority Data

Jun. 22, 1978 [FR] France .................. 78 18693

[51] Int. Cl.³ ............... C07C 149/42; A61K 31/195
[52] U.S. Cl. ...................... 424/309; 560/18; 560/103; 562/432; 424/319; 260/465 D
[58] Field of Search .............. 424/309, 319; 560/18; 562/432

[56] References Cited

FOREIGN PATENT DOCUMENTS 7960M 6/1970 France .

Primary Examiner—Natalie Trousof
Assistant Examiner—Michael Shippen
Attorney, Agent, or Firm—Cushman, Darby & Cushman

[57] ABSTRACT

L-cysteine derivatives of formula

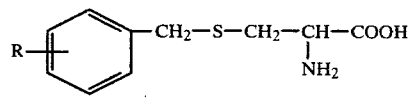

in which R is a lower alkoxycarbonyl or carboxy group, and salts thereof. The compounds have been found to have a mucolytic activity and low toxicity. Processes for the preparation of the compounds and medicaments containing them are described and exemplified.

13 Claims, No Drawings

L-CYSTEINE DERIVATIVES AND MEDICAMENTS CONTAINING THEM

The present invention relates to novel L-cysteine derivatives, to a process for the preparation thereof and to uses thereof in human and veterinary medicine as well as in cosmetics.

The derivatives of the invention conform to the general formula:

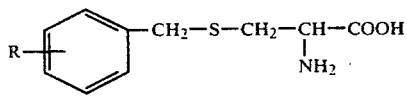
(I)

in which R represents a lower alkoxycarbonyl group (especially with $C_2$ to $C_8$) or a carboxy group.

The invention also includes the pharmaceutically acceptable inorganic or organic salts of the derivatives of formula (I).

The object of the invention is also a process for the preparation of the compounds of formula (I), characterised in that the L-cysteine of formula:

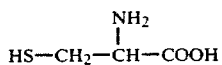

is condensed with a halogenated derivative of formula:

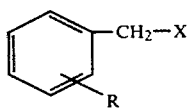
(II)

in which R represents the cyano or alkoxycarbonyl group and X represents a halogen such as, for example chlorine or bromine, thus obtaining the derivatives of formula (I) in which R represents the alkoxycarbonyl group or cyano derivatives which can also be obtained as described in French BSM 7960 M.

Condensation is effected at ambient temperature under a protective nitrogen atmosphere in hydroalcoholic solution, especially lower hydroalkanolic solution, in the presence of an alkali metal hydroxide, especially sodium hydroxide.

Those of the derivatives (I) in which R is the carboxy group are obtained by acid hydrolysis of the corresponding derivatives (I) in which R is the cyano or alkoxycarbonyl group. The reaction is effected by heating, especially at reflux, of these compounds in a strongly diluted inorganic acid such as hydrochloric acid, hydrobromic acid or sulphuric acid.

The derivatives (II) in which R represents CN are commercial products. Those in which R is alkoxycarbonyl have been prepared by the processes described in the literature, for example according to P. E. Hanna et al., "J. Med. Chem.", 1974, 17, 1020.

The following non-limiting Examples illustrate the invention.

EXAMPLE 1

S-(o-methoxycarbonylbenzyl)cysteine

Nitrogen is bubbled into a stirred solution of 8.65 grams (49.25 mmol) of monohydrated L-cysteine hydrochloride in 16 cc of water. 49.25 cc (98.5 mmol) of 2 N sodium hydroxide, followed by a solution of 11.3 grams (49.25 mmol) of methyl α-bromo-o-toluate in 100 cc of methanol are introduced dropwise, maintaining the temperature between 0° and 5° C. Bubbling of nitrogen is maintained and stirring is continued at 5° C. for 1 hour (the deposit of an oily phase on the walls is observed and this solidifies rapidly into white crystals), then at ambient temperature for 20 minutes. The mixture is evaporated to dryness and the residue is recrystallised directly in a mixture of 110 cc of water and 30 cc of methanol. The white crystals obtained (9.25 grams, yield 70%) melt with a release of gas at 210° C.

EXAMPLE 2

S-(o-carboxybenzyl)cysteine

A solution of 7.65 grams (28.4 mmol) of S-(o-methoxycarbonylbenzyl)cysteine in 100 cc of 6 N hydrochloric acid is refluxed for 2 hours and 30 minutes under a nitrogen atmosphere. The solution is evaporated to dryness and the residue is dissolved in a minimum of water and brought to a pH value of 2.5 to 3 by the addition of sodium hydroxide. The white crystals obtained are filtered and dried in vacuo. Melting point 240° to 245° C. (decomposition) (4 grams, yield 55%).

This compound gives a monosodium salt, m.p. 252° to 254° C., (ethanol-water), slightly hygroscopic, highly soluble in water.

EXAMPLE 3

S-(m-cyanobenzyl)L-cysteine

Prepared by the process described in Example 1 from m-cyanobenzyl bromide.

Methane sulphonate, white crystals, m.p. 130°–135° C., (ethanol-isopropanol), slightly hygroscopic, yield 44.5%.

EXAMPLE 4

S-(p-cyanobenzyl) L-cysteine

Prepared by the process described in Example 1 from p-cyanobenzyl bromide.

Base: white crystals, m.p. 171° C., (ethanol-isopropanol), yield 10%.

EXAMPLE 5

S-(m-carboxybenzyl) L-cysteine

Prepared by the process described in Example 2 by refluxing of S-(m-cyanobenzyl) L-cysteine (Example 3) in 12 N hydrochloric acid.

Base: pink crystals, m.p. >260° C., (dimethyl formamide), yield 64%.

EXAMPLE 6

S-(p-carboxybenzyl) L-cysteine

Prepared by the process described in Example 2 by refluxing of S-(p-cyanobenzyl) L-cysteine (Example 4) in 12 N hydrochloric acid.

Base: pink crystals, m.p. >260° C., (dimethyl formamide), yield 84%. This compound gives a monosodium salt, m.p. >260° C. (ethanol-water), slightly hygroscopic, highly soluble in water.

The toxicological and pharmacological investigation reported hereinafter showed that the derivatives of the invention possessed remarkable mucolytic properties, while being completely devoid of toxicity.

The object of the invention is therefore also a medicament having especially a mucolytic activity, characterised in that it contains as active ingredient a derivative of formula (I) or a pharmaceutically acceptable salt thereof.

Furthermore, it was verified that the derivatives of the invention are endowed with trophic properties towards the skin and play a protective role in respect of the epidermis, the nails and the hair.

I Toxicological study

The compounds of the invention benefit from a very low acute toxicity. Thus, the LD 50/24h/kg of body weight, determined in mice by the method of Miller and Tainter, for the oral route is more than 3 grams.

Furthermore, tests conducted with various animal species on acute, chronic, sub-chronic and delayed toxicity have not disclosed any local or general reaction whatever, disturbance of the weight development of the animals, disturbance in the regularly effected biological controls or an anomaly in the microscopic and macroscopic examinations of the organs sampled.

II Pharmacological study

This study of the mucolytic activity of the derivatives of the invention was conducted by the method described by Andre Quevauvilliers, Suzanne Garcet and Vu Ngcoc Huyen (Pharmaceutical Products and Problems, 27, 267–280, 1972) which consists in causing in rats by the inhalation of irritant gases lesions of the respiratory mucous membrane and, simultaneously, bronchial hypersecretion.

Thus, the rats are subjected to the inhalation of sulphur dioxide ($SO_2$) at a concentration of 300 ppm, 4 hours a day, 5 days a week, for 8 weeks. During the first 4 weeks the animals receive no treatment.

During the 4 following weeks, with the animals of batch A (control) continuing to receive no treatment, the animals of batch B (treated control) receive 500 mg/kg of S-carboxymethyl cysteine and the animals of batch C (treated) receive 500 mg/kg of the derivative to be tested.

24 hours after treatment has stopped the animals are killed and the lungs and bronchial tubes are extracted. After a solution of Alcian blue is injected into the main bronchial tube, macroscopic sections are made. The examination by means of a binocular magnifying glass enables the secretory state of the mucous membrane of the bronchial tree to be established. The hypersecretion, when it exists, partially or completely obstructs the main and secondary bronchial tubes. When it is total, the obstruction may be constituted by a compact plug, nodulous accumulations or bulbous accumulations.

The results are collated in the following table, the values expressed being average values arrived at within each batch (percentages).

|  | Compact plug | Nodulous accumulation | Bulbous accumulation | Complete obstruction | Partial obstruction | Total and partial obstruction |
|---|---|---|---|---|---|---|
| $SO_2$ | 51 | 8 | 3 | 63 | 9 | 72 |
| S-carboxymethyl cysteine | 10 | 2 | | 12 | 8 | 20 |

-continued

|  | Compact plug | Nodulous accumulation | Bulbous accumulation | Complete obstruction | Partial obstruction | Total and partial obstruction |
|---|---|---|---|---|---|---|
| teine | | | | | | |
| Derivative 1 | 7 | 3 | | 10 | 8 | 18 |
| Derivative 2 | 8 | 2 | 1 | 11 | 8 | 19 |
| Derivative 5 | 10 | 2 | | 12 | 5 | 17 |
| Derivative 6 | 8 | 3 | | 11 | 6 | 17 |

The results of these studies reveal the high tolerance and low toxicity of the derivatives of the invention as well as their remarkable mucolytic activity which make them very useful in human and veterinary medicine.

The medicament of the invention can therefore be presented for oral administration in the form of tablets, coated tablets, capsules and syrup. It can also be presented for external use in the form of drops or nasal sprays.

Each unit dose advantageously contains 0.050 grams to 1.0 grams of active ingredient, the doses administered daily varying between 0.050 grams and 3 grams depending on the seriousness of the condition treated and on the age of the patient. For external use the solutions employed contain advantageously 2 to 5% of active ingredient.

Some pharmaceutical formulations of the medicament of the invention are given hereinafter y way of non-limiting example.

Coated tablets

Derivative No. 2: 0.500 grams.

Excipient: cellulose, sodium carboxymethyl cellulose, magnesium stearate, talcum, stearic acid, colophony, essence of turpentine, shellac, gelatine, sugar, talcum, white wax, titanium oxide, erythrosine.

Nasal drops

Derivative No. 5: 2.00 grams.

Aqueous excipient sufficient to make 100 millilitres.

For their use in cosmetics the derivatives of the invention can be mixed with suitable pharmaceutically acceptable solid or liquid vehicles and presented in the form of cream, ointment or lotion.

The studies which have just been reported show the remarkable mucolytic action of the derivatives of the invention which represent a selective therapeutic agent of conditions of the respiratory mucous membrane. By lysis action on the pathological secretions they facilitate expectoration and clear the respiratory tracts. On the other hand, they contribute to reestablishing the physiological secretion of mucus and thus to protecting the respiratory tracts.

They are indicated in pneumology in chronic bronchitis, tracheo-bronchitis, bronchorrhea and in oto-rhino-laryngology in otitis, sinusitis, pharyngitis and rhino-pharyngitis.

What we claim is:

1. L-cysteine compound of the formula

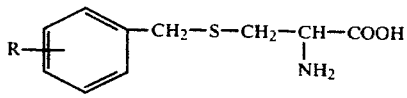

in which R is lower alkoxycarbonyl or carboxy or a pharmaceutically acceptable salt thereof.

2. The compound of claim 1, which is S-(o-methoxycarbonylbenzyl) cysteine.

3. The compound of claim 1, which is S-(o-carboxybenzyl) cysteine.

4. The compound of claim 1, which is S-(m-carboxybenzyl) cysteine.

5. The compound of claim 1, which is S-(p-carboxybenzyl) cysteine.

6. A mucolytic medicament comprising a pharmaceutically acceptable carrier and an effective amount of the compound of claim 1.

7. The medicament of claim 6 wherein said compound is present in an amount of 2 and 5 percent by weight.

8. A unit dose of the medicament of claim 6 containing 0.050 to 1.0 g of said compound.

9. The medicament of claim 6 wherein said compound is S-(o-methoxycarbonylbenzyl) cysteine.

10. The medicament of claim 6 wherein said compound is S-(o-carboxybenzyl) cysteine.

11. The medicament of claim 6 wherein said compound is S-(m-carboxybenzyl) cysteine.

12. The medicament of claim 6 wherein said compound is S-(p-carboxybenzyl) cysteine.

13. A process for facilitating expectoration, for clearing the respiratory tract, for reestablishing the physiological secretion of mucus and for protecting the respiratory tract comprising administering an effective amount of the medicament of claim 6.

* * * * *